United States Patent

Bruder

Patent Number: 6,120,469
Date of Patent: Sep. 19, 2000

[54] CAST VENTILATION SYSTEM

[76] Inventor: Michael R. Bruder, 1222 Vista Dr., Fenton, Mich. 48430

[21] Appl. No.: 09/035,496

[22] Filed: Mar. 5, 1998

[51] Int. Cl.[7] ..................................................... A61F 5/00
[52] U.S. Cl. ..................................... 602/13; 602/6; 602/9
[58] Field of Search ................... 602/6, 13, 8; 493/269; 4/632, 633, 634, 635, 636, 116; 428/582

[56] References Cited

U.S. PATENT DOCUMENTS

| | | |
|---|---|---|
| 2,704,067 | 3/1955 | Moses . |
| 4,898,160 | 2/1990 | Brownlee . |
| 5,102,130 | 4/1992 | Lichtwardt . |

*Primary Examiner*—John G. Weiss
*Assistant Examiner*—K. Hart
*Attorney, Agent, or Firm*—Gifford, Krass, Groh, Sprinkle, Anderson & Citkowski, P.C.

[57] ABSTRACT

A ventilation system is disclosed for a cast of the type which encompasses a limb with a rigid material such that an inside surface of the cast faces the limb while an outside surface of the cast is spaced outwardly from the inside surface. The ventilation system includes a tube insertable through the cast so that one end of the tube is open to the limb while the other end of the tube is open to the outside surface of the cast. A source of pressurized air is then fluidly connected to the other or outside end of the tube thus forcing air flow through the tube and into the area between the inside surface of the cast and the limb.

3 Claims, 1 Drawing Sheet

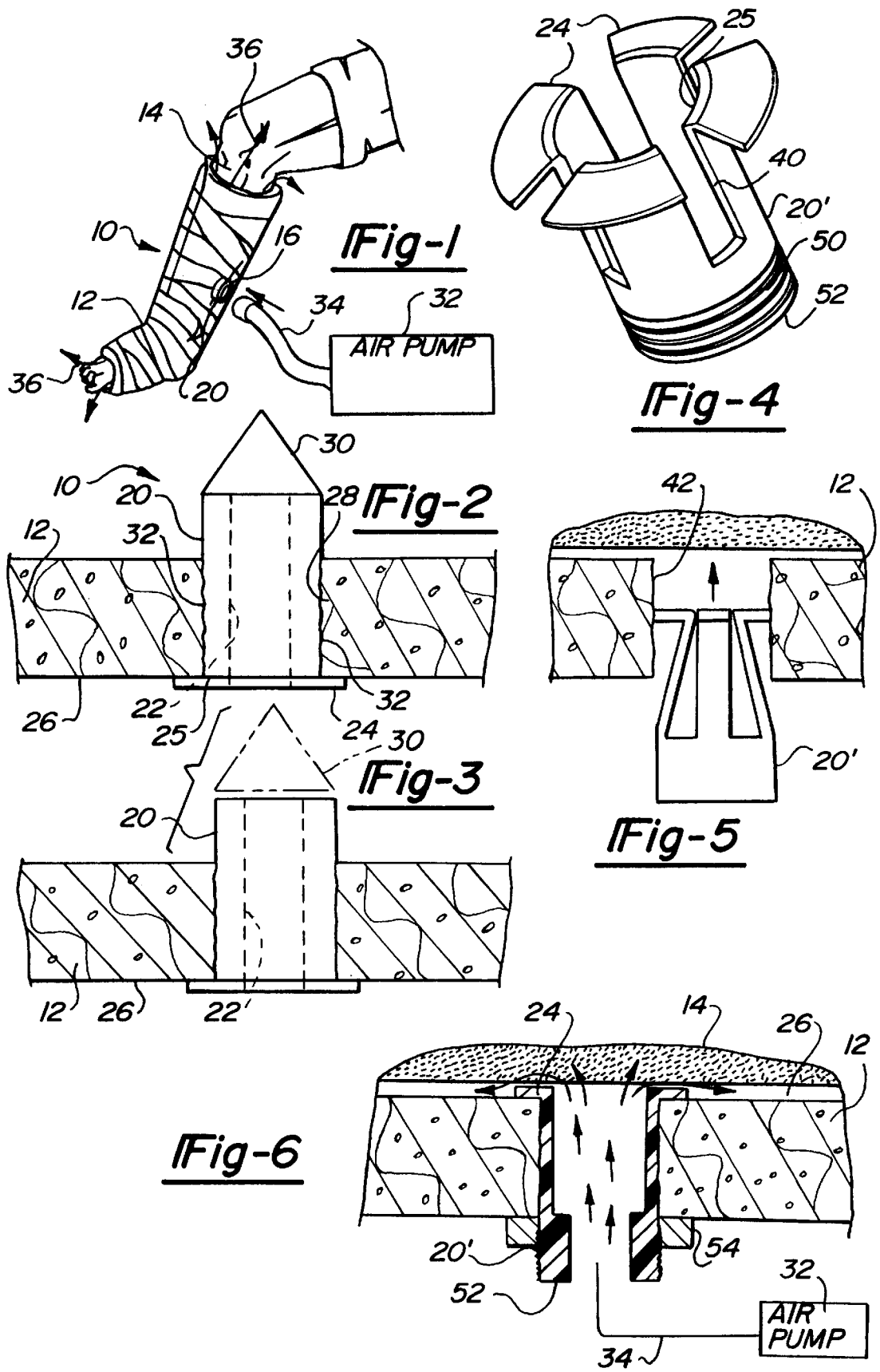

CAST VENTILATION SYSTEM

BACKGROUND OF THE INVENTION

I. Field of the Invention

The present invention relates to a ventilation system for a cast.

II. Description of the Prior Art

Whenever a limb, such as a leg or arm, is broken, the limb is typically placed in a cast in order to hold the limb rigid while the broken bone or other injury mends. These previously known casts typically are constructed from a gauze material wrapped around the limb which is then in turn covered with a rigid material, such as plaster. The rigid material, of course, forms the cast to hold the limb against movement such that an inside surface of the cast faces towards the limb while the outside surface is outwardly spaced from the inside surface and faces outwardly.

One common problem associated with a cast placed over a broken limb occurs when the area between the inside surface of the cast and the limb becomes wet. When this occurs, an itching sensation of the broken limb results. However, since the cast encompasses the broken limb, the limb cannot be easily or effectively scratched.

SUMMARY OF THE PRESENT INVENTION

The present invention provides a ventilation system for a cast which overcomes the above-mentioned disadvantages of the previously known devices.

In brief, the ventilation system of the present invention comprises a tube insertable through an opening in the cast so that one end of the tube is open to the limb while the other end of the tube is open to the outside surface of the cast. A source of pressurized air is then fluidly connected to the outer end of the tube so that, upon activation of the pressurized air source, the pressurized air source blows air into the area between the inside of the cast and the limb. This air flow, furthermore, effectively dries or removes any moisture which may be present on the inside surface of the cast.

In one embodiment of the invention, the tube is insertable after complete formation of the cast. In still another embodiment of the invention, the tube is placed on the broken limb and the cast is formed around the tube.

BRIEF DESCRIPTION OF THE DRAWING

A better understanding of the present invention will be had upon reference to the following detailed description when read in conjunction with the accompanying drawing, wherein like reference characters refer to like parts throughout the several views, and in which:

FIG. 1 is a elevational diagrammatic view illustrating a preferred embodiment of the present invention;

FIG. 2 is a fragmentary longitudinal sectional view illustrating a first preferred embodiment of the present invention;

FIG. 3 is an exploded view similar to FIG. 2;

FIG. 4 is an elevational view illustrating a second preferred embodiment of the present invention;

FIG. 5 is a fragmentary sectional view illustrating the insertion of the second preferred embodiment into an opening formed in the cast; and FIG. 6 is a longitudinal sectional view of the second preferred embodiment of the present invention.

DETAILED DESCRIPTION OF PREFERRED EMBODIMENTS OF THE PRESENT INVENTION

With reference first to FIG. 1, a preferred embodiment of the cast ventilation system 10 of the present invention is there shown for use with a cast 12 positioned around a broken limb 14, such as a leg. In the conventional fashion, the cast 12 is made of a rigid material which prevents movement of the limb 14 while the bone or other injury heals.

Referring now to FIG. 2, the ventilation system 10 is there shown in greater detail and comprises an elongated tube 20 having an internal bore 22. The tube 20 is preferably cylindrical in shape although other shapes can alternatively be used.

Still referring to FIG. 2, an outwardly extending flange 24 is provided at an inner end 25 of the tube 20 and this flange 24 abuts against an inside surface 26 of the cast 12. The inside surface 26, in turn, faces the patient limb 14 (FIG. 1).

The tube 20 extends entirely through an opening 28 formed through the cast 12 and preferably includes a cone 30 coaxially formed at its outer end. The tube 20 also preferably includes a plurality of serrations 32 formed on its other periphery. These serrations 32 enhance the mechanical grip between the tube 20 and the cast 12.

With reference now to FIGS. 2 and 3, the embodiment of the tube 20 shown in FIGS. 2 and 3 is intended for use when the tube 20 is cast into position during the formation of the cast. When this occurs, the flange 24 is positioned against the user's limb and the wrapping forming the cast is then wrapped around the user's limb. As the wrapping is positioned over the tube 20, the cone 30 punches a hole in the wrapping such that the tube 20 is cast in place during the formation of the cast 12.

After the cast 12 is then completely formed, the cone 30 is removed by cutting from the tube 20 as shown in FIG. 3. Upon removal of the cone, the passageway 22 formed through the tube 20 extends entirely from the outer surface and to the inner surface 26 of the cast 12. With reference again to FIG. 1, with the tube 20 secured to the cast 12 as previously described, a source of pressurized air, such as an air pump 32, is then connected by a housing 34 to the outer end of the tube 20. Upon activation of the air pump, the air pump 32 pumps air through the tube 20 and into the area between the inside surface 26 of the cast 12 and the user's limb 14. The air then exits through the ends of the cast 12, as indicated by arrows 36, which dries or removes any moisture which may be present between the cast and the user's limb.

With reference now to FIGS. 4–6, a second preferred embodiment of the invention is there shown in which the tube 20' is not cast in situ during the formation of the cast 12, but rather installed after the cast has already hardened. In this embodiment of the invention, the tube 20' includes a plurality of circumferentially spaced and longitudinally extending slots 40 which extend from the inside end 25 of the tube 20' and to a midpoint of the tube 20'. In doing so, the slots 40 divide the flange 24 into a plurality of flange sections.

The tube 20' is preferably of a one piece plastic construction such that the tube 20' is made of a resilient material. Thus, in order to install the tube 20' into the cast 12, a hole 42 is first formed through the cast 12 as shown in FIG. 5. The flange segments 24 are then compressed together as shown in FIG. 5 thus allowing passage of the flange segment through the cast opening 42.

With reference now to FIG. 6, after complete insertion of the tube 20' into the opening 42 such that the flange segments 24 pass completely through the cast opening 42, the flange section 24, due to the resiliency of the tube 20', expands outwardly such that the flange segments 24 abut against the inside surface 26 of the cast 12. In doing so, the flange segments 24 retain the tube 20 to the cast 12 in the desired fashion. The air pump 32 is then fluidly connected by the hose 34 to the outer end of the tube 20' in order to remove moisture between the cast 12 and the limb 14.

Preferably the tube 20' includes external threads 50 about its end 52 opposite from the flange segments 24. A nut 54 (FIG. 6) threadably cooperates with the tube threads 50 to secure the tube 20' to the cast 12.

From the foregoing, it can be seen that the present invention provides a simple and yet effective ventilation system for a cast to remove moisture which may be entrapped between the cast and the user's limb. Having described my invention, however, many modifications thereto will become apparent to those skilled in the art to which it pertains without deviation from the spirit of the invention as defined by the scope of the appended claims.

I claim:

1. A ventilation system for a cast of the type which encompasses a limb with a rigid material such that an inside surface of the cast faces the limb while an outside surface of the cast is spaced outwardly from the inside surface, said ventilation system comprising:

a tube insertable through said cast so that one end of said tube is open to the limb while the other end of the tube is open to the outside surface of the cast, a source of pressurized air, means for connecting said source of pressurized air to said other end of said tube, a plurality of flange sections which extend outwardly from said one end of said tube, sad tube including a longitudinally extending slot open to said one end of said tube between each adjacent pair of flange sections, wherein said tube is constructed of a resilient material so that, upon compression of said flange sections together, said flange sections are insertable through an opening in the cast and so that, after passage through the cast opening, said flange members expand outwardly and engage the inner surface of the cast and a nut which threadably engages said tube so that the cast is sandwiched in between said flange sections and said nut.

2. The invention as defined in claim 1 wherein said tube is cylindrical in shape.

3. The invention as defined in claim 1 wherein said tube is made of a plastic material.

\* \* \* \* \*